United States Patent
Fogg et al.

(10) Patent No.: US 8,834,788 B2
(45) Date of Patent: Sep. 16, 2014

(54) METHOD FOR SANITIZING/STERILIZING A CONTAINER/ENCLOSURE VIA CONTROLLED EXPOSURE TO ELECTROMAGNETIC RADIATION

(75) Inventors: Benjamin Fogg, Holland, MI (US); David Hofferbert, Holland, MI (US)

(73) Assignee: Fogg Filler Company, Holland, MI (US)

( * ) Notice: Subject to any disclaimer, the term of this patent is extended or adjusted under 35 U.S.C. 154(b) by 542 days.

(21) Appl. No.: 11/417,826

(22) Filed: May 4, 2006

(65) Prior Publication Data
US 2007/0258851 A1 Nov. 8, 2007

(51) Int. Cl.
| B01J 19/00 | (2006.01) |
|---|---|
| B01J 19/08 | (2006.01) |
| G01N 23/00 | (2006.01) |
| A61N 5/00 | (2006.01) |
| B65B 55/08 | (2006.01) |
| A61L 2/10 | (2006.01) |

(52) U.S. Cl.
CPC .. *A61L 2/10* (2013.01); *B65B 55/08* (2013.01)
USPC .......... 422/24; 422/40; 422/186; 250/454.11; 250/455.11; 250/492.1

(58) Field of Classification Search
CPC .......... A01N 1/0294; A61L 2/00; A61L 9/18; A61L 9/20; B65B 55/00
USPC ......... 422/22, 24, 40, 186, 186.3; 250/432 R, 250/454.11, 455.11, 492.1
See application file for complete search history.

(56) References Cited

U.S. PATENT DOCUMENTS

| 2,072,417 A | 3/1937 | Berndt et al. |
|---|---|---|
| 3,817,703 A | 6/1974 | Atwood |
| 3,941,670 A | 3/1976 | Pratt, Jr. |
| 4,443,533 A | 4/1984 | Panico |
| 4,464,336 A | 8/1984 | Hiramoto |
| 4,495,040 A | 1/1985 | Panico |
| 4,871,559 A | 10/1989 | Dunn et al. |
| 5,144,146 A | 9/1992 | Wekhof |
| 5,364,645 A | 11/1994 | Lagunas-Solar et al. |
| 5,489,442 A | 2/1996 | Dunn et al. |
| 5,533,441 A | 7/1996 | Reznik et al. |
| 5,549,041 A | 8/1996 | Zhang et al. |
| 5,562,024 A | 10/1996 | Polny, Jr. |
| 5,571,335 A | 11/1996 | Lloyd |
| 5,571,550 A | 11/1996 | Polny, Jr. |
| 5,583,960 A | 12/1996 | Reznik |
| 5,607,613 A | 3/1997 | Reznik |
| 5,607,711 A | 3/1997 | Lagunas-Solar |
| 5,609,900 A | 3/1997 | Reznik |
| 5,630,360 A | 5/1997 | Polny, Jr. |
| 5,636,317 A | 6/1997 | Reznik |
| 5,658,530 A | 8/1997 | Dunn |
| 5,662,031 A | 9/1997 | Qin et al. |
| 5,670,198 A | 9/1997 | Reznik et al. |
| 5,741,539 A | 4/1998 | Knipper et al. |

(Continued)

*Primary Examiner* — Monzer R Chorbaji
(74) *Attorney, Agent, or Firm* — King & Partners, PLC

(57) ABSTRACT

A method for sanitizing/sterilizing a container/enclosure for use in the food industry or the beverage industry comprising the steps of: providing a container and/or enclosure; providing an electromagnetic radiation source; controllably exposing the container and/or enclosure to electromagnetic radiation from the electromagnetic radiation source for a period of time; and at least one of sanitizing and sterilizing at least a portion of the container and/or enclosure with the electromagnetic radiation.

28 Claims, 1 Drawing Sheet

(56) References Cited

U.S. PATENT DOCUMENTS

| | | | |
|---|---|---|---|
| 5,758,015 A | 5/1998 | Polny, Jr. |
| 5,768,472 A | 6/1998 | Reznik |
| 5,768,853 A | 6/1998 | Bushnell et al. |
| 5,771,336 A | 6/1998 | Polny, Jr. |
| 5,776,529 A | 7/1998 | Qin et al. |
| 5,786,598 A | 7/1998 | Clark et al. |
| 5,837,040 A | 11/1998 | Caughron et al. |
| 5,863,580 A | 1/1999 | Reznik |
| 5,900,211 A | 5/1999 | Dunn et al. |
| 5,925,885 A | 7/1999 | Clark et al. |
| 5,958,271 A | 9/1999 | Westerberg et al. |
| 5,990,454 A | 11/1999 | Westerberg et al. |
| 6,013,900 A | 1/2000 | Westerberg et al. |
| 6,013,918 A | 1/2000 | Bushnell et al. |
| 6,019,031 A | 2/2000 | Qin et al. |
| 6,045,845 A | 4/2000 | Gundt |
| 6,054,097 A | 4/2000 | Mass et al. |
| RE36,724 E | 6/2000 | Westerberg et al. |
| 6,093,432 A | 7/2000 | Mittal et al. |
| 6,132,784 A | 10/2000 | Brandt et al. |
| 6,228,332 B1 | 5/2001 | Dunn et al. |
| 6,264,836 B1 | 7/2001 | Lantis |
| 6,287,481 B1 | 9/2001 | Luthra et al. |
| 6,312,931 B1 | 11/2001 | O'Dwyer et al. |
| 6,329,136 B1 | 12/2001 | Lagunas-Solar et al. |
| 6,331,321 B1 | 12/2001 | Robbins |
| 6,433,344 B1 | 8/2002 | Salisbury et al. |
| 6,449,923 B1 * | 9/2002 | Cook et al. ............... 53/400 |
| 6,465,799 B1 | 10/2002 | Kimble et al. |
| 6,517,776 B1 * | 2/2003 | Rodgers et al. ............ 422/24 |
| 6,565,803 B1 | 5/2003 | Bolton et al. |
| 6,566,659 B1 * | 5/2003 | Clark et al. ........... 250/455.11 |
| 6,592,816 B1 | 7/2003 | Ebel et al. |
| 6,599,487 B1 | 7/2003 | Luthra et al. |
| 6,632,408 B1 | 10/2003 | Luthra et al. |
| 6,692,694 B1 | 2/2004 | Curry et al. |
| 6,730,923 B1 | 5/2004 | May et al. |
| 6,787,105 B2 | 9/2004 | Robbins |
| 6,843,961 B2 | 1/2005 | Hlavinka et al. |
| 6,951,617 B2 | 10/2005 | Fries et al. |
| 7,038,219 B2 | 5/2006 | Clark et al. |
| 7,081,636 B2 | 7/2006 | Moruzzi |
| 7,091,495 B2 | 8/2006 | Panico et al. |
| 2003/0044311 A1 | 3/2003 | Sousa et al. |
| 2004/0052702 A1 | 3/2004 | Shuman et al. |
| 2005/0053642 A1 | 3/2005 | Ulbricht et al. |
| 2005/0199483 A1 | 9/2005 | Kroll |

\* cited by examiner

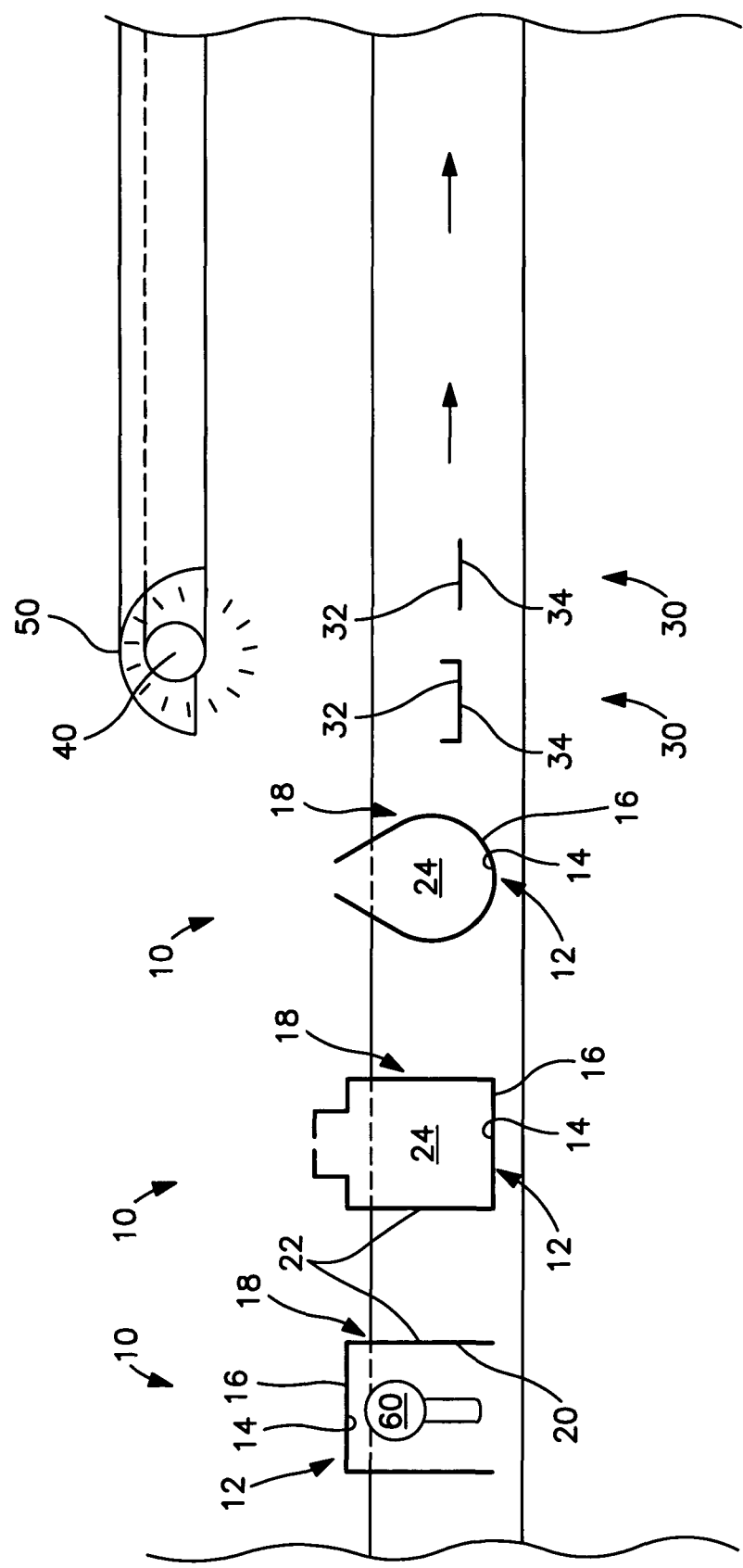

METHOD FOR SANITIZING/STERILIZING A CONTAINER/ENCLOSURE VIA CONTROLLED EXPOSURE TO ELECTROMAGNETIC RADIATION

CROSS-REFERENCE TO RELATED APPLICATIONS

Not Applicable

BACKGROUND OF THE INVENTION

1. Field of the Invention

The present invention relates in general to a method for sanitizing/sterilizing a container and/or enclosure and, more particularly, to a method for sanitizing and/or sterilizing a container and/or enclosure via, for example, controlled exposure to high-intensity, pulsed electromagnetic radiation, including predetermined wavelengths of ultraviolet radiation.

2. Background Art

Containers, such as bottles, cans, cartons, etcetera and associated enclosures, such as caps, lids, covers, tabs, etcetera for use in association with the food and beverage industries have been known in the art for more than a century. Methods for sanitizing and/or sterilizing such containers/enclosures are likewise well known and have evolved over several decades.

For example, one conventional method for sanitizing and/or sterilizing a container prior to filling with a food or beverage product is to wash the container with an aqueous solution containing surfactants, anti-bacterial agents, anti-microbial agents, and/or anti-septic agents—just to name a few. Typically a container that has been exposed to such harsh chemicals, during a wash cycle, is subsequently rinsed one or more times in an attempt to remove any residual chemicals that were introduced into the container during a wash and/or rinse cycle.

While the above-identified conventional method for sanitizing and/or sterilizing a container is effective from a cleaning perspective, utilizing such a method is problematic for a plurality of reasons. By way of example, customer requirements regarding residual contamination from the wash cycle place extraordinary pressure upon filler device manufacturers to generate filler devices and associated operational standards which completely eliminate any wash cycle residual contamination. Essentially customers are requiring that, immediately prior to filling, the container is "neat" or free from even a single droplet of residual contamination—including water. To be sure, complying with such industry demands, whether initiated by a customer or by local, state and/or federal regulations has placed a premium on efficiently adapting to many pre-filling requirements. Obviously, the requirement of providing a "neat" or "nearly neat" container can be incredibly difficult with certain container configurations which have geometric shapes that enhance entrapment of residual fluids. By way of example, many bottles have inner peripheral geometries with curves and/or angles which facilitate retention of residual contamination—especially if the contaminant is water which has relatively "sticky" or relatively high adhesive properties.

The above-identified conventional sanitizing/sterilizing method is also very time consuming, creates environmental problems with regard to chemical waste disposal, and is expensive, thereby rendering it highly undesirable for a plurality of reasons.

It is therefore an object of the present invention to provide a method for sanitizing and/or sterilizing a container and/or enclosure via, for example, controlled exposure to high-intensity, pulsed electromagnetic radiation, including predetermined wavelengths of ultraviolet radiation to remedy and/or minimize the aforementioned problems and/or complications associated with conventional sanitizing and/or sterilizing methods for containers in the food and/or beverage industry.

These and other objects of the present invention will become apparent in light of the present specification, claims, and drawings.

SUMMARY OF THE INVENTION

The present invention is directed to a method for sanitizing/sterilizing a container for use in the food industry or the beverage industry, comprising the steps of: (a) providing a container suitable for filling with food and/or beverage, wherein the container comprises: (1) a base having an inner surface and an outer surface; (2) at least one side wall having an inner surface and an outer surface; and (3) a containment region defined at least by the inner surface of the base and the inner surface of the at least one side wall; (b) providing an electromagnetic radiation source; (c) controllably exposing the containment region of the container to electromagnetic radiation from the electromagnetic radiation source for a period of time; and (d) at least one of sanitizing and/or sterilizing the containment region of the container with the electromagnetic radiation.

In a preferred embodiment of the present invention, the step of providing an electromagnetic radiation source comprises providing an electromagnetic radiation source which is substantially mercury free as well as substantially free from generating ozone during operation of the same.

In another preferred embodiment of the present invention, the step of controllably exposing the containment region of the container to electromagnetic radiation for a period of time comprises controllably exposing the containment region with pulsed electromagnetic radiation. In this embodiment the pulse duration is preferably less than approximately 5 milliseconds, and more preferably less than approximately 2 milliseconds. Such controlled exposure may include reflected and/or non-reflected external and/or internal exposure of the containment region relative to the electromagnetic radiation source.

In yet another aspect of the present invention, the containment region is preferably exposed to electromagnetic radiation for a total duration of less than approximately 30 seconds, and more preferably less than approximately 5 seconds.

In accordance with present invention, the containment region is preferably exposed to pulsed electromagnetic radiation having a percent transmission of less than approximately 80% at below approximately 240 nanometers to, in turn, facilitate avoiding undesired generation of any material amount of ozone. In this embodiment the predominant wavelength of electromagnetic radiation is preferably between approximately 240 nanometers and approximately 400 nanometers, and more preferably predominantly UV-B electromagnetic radiation (circa 254 nm).

In another embodiment of the present invention, the step of sanitizing and/or sterilizing the containment region of the container with the electromagnetic radiation includes the step of providing a greater than approximately 3 Log reduction in undesirable matter in less than approximately 1 to approximately 10 seconds, and more preferably a 5 Log reduction in undesirable matter in less than approximately 3 to approximately 20 seconds, and most preferably a 5 Log reduction in undesirable matter in less than approximately 3 seconds.

In a further embodiment of the present invention, a reflective element (e.g. a substantially spherical reflective element) is provided for association within the container to enhance sanitization and/or sterilization of the containment region.

The present invention is also directed to a method for sanitizing/sterilizing an enclosure (e.g. cap) associable with a container for use in the food industry or the beverage industry, comprising the steps of: (a) providing an enclosure associable with a container suitable for filling with at least one of food and beverage, wherein the enclosure comprises an inner surface and an outer surface; (b) providing an electromagnetic radiation source; (c) controllably exposing at least one of the inner surface and the outer surface of the enclosure to electromagnetic radiation from the electromagnetic radiation source for a period of time; and (d) at least one of sanitizing and sterilizing at least one of the inner surface and the outer surface of the enclosure with the electromagnetic radiation.

The present invention is also directed to a method for sanitizing/sterilizing a container and enclosure for use in the food industry or the beverage industry, comprising the steps of: (a) providing a container suitable for filling with at least one of food and beverage wherein the container comprises: (1) a base having an inner surface and an outer surface; (2) at least one side wall having an inner surface and an outer surface; and (3) a containment region defined at least by the inner surface of the base and the inner surface of the at least one side wall; (b) providing an enclosure associable with the container wherein the enclosure comprises an inner surface and an outer surface; (c) providing an electromagnetic radiation source; (c) controllably exposing the containment region of the container and at least one of the inner surface and the outer surface of the enclosure to electromagnetic radiation from the electromagnetic radiation source for a period of time; and (d) at least one of sanitizing and sterilizing the containment region of the container and at least one of the inner surface and the outer surface of the enclosure with the electromagnetic radiation.

BRIEF DESCRIPTION OF THE DRAWINGS

The invention will now be described with reference to the drawings wherein:

FIG. 1 of the drawings is a schematic representation of a container and/or enclosure sanitized/sterilized in accordance with the present invention.

DETAILED DESCRIPTION OF THE INVENTION

While this invention is susceptible of embodiment in many different forms, there will herein be described in detail several specific embodiments with the understanding that the present disclosure is to be considered as an exemplification of the principles of the invention and is not intended to limit the invention to the embodiments illustrated.

In accordance with the present invention, and as is shown in FIG. 1, a method for sanitizing/sterilizing a container 10 (e.g. a can, bottle, carton, etcetera) and/or an enclosure 30 (e.g. a cap, lid, cover, tab, etcetera) for use in the food industry or the beverage industry is disclosed which comprises a plurality of steps, the order of which is not paramount to the success of the invention. It will be understood that FIG. 1 is merely a schematic representation of an embodiment of the present invention. As such, some of the components have been distorted from their actual scale for pictorial clarity.

First, a food or beverage container and/or enclosure is provided. A typical container generally includes a surface or ground engaging base 12 having an inner surface 14 and an outer surface 16, one or more side walls 18 (e.g. two, three, four, five, ten—just to name a few) each having inner surfaces 20 and outer surfaces 22, and a containment region 24 which is generally defined by the base and the side wall(s), and optionally a top and/or cap. A typical enclosure generally includes an inner surface 32 and an outer surface 34. It will be understood that any one of a number of containers and/or enclosures are suitable for use in association with the present invention. Indeed, the only limitation being that the container and/or enclosure must be capable of being sanitized and/or sterilized with an electromagnetic radiation source.

Second, an electromagnetic radiation source 40 is provided, such as a pulsed ultraviolet (UV) source which is commercially available from, among other sources, Xenon Corporation. Preferably the electromagnetic radiation source emits radiation predominantly between approximately 240 nanometers and approximately 400 nanometers, and is preferably predominantly UV-B radiation. It will be understood that the electromagnetic radiation source may optionally be associated with a reflective element or member 50 (e.g. a parabolic mirror).

A pulsed wave energy source is important to the present invention because conventional, continuous wave operation generated from, for example, mercury lamps and others that use gamma radiation are problematic from both heat and toxicity perspectives. Examples of preferred pulse durations are less than approximately 5 milliseconds, and more preferably less than approximately 2 milliseconds. In addition to the radiation source preferably being "pulsed," as compared to continuous, it is preferred that the electromagnetic radiation source be substantially free from generating toxic ozone during operation of the same. It will be understood that one way to generally preclude the generation of ozone is to utilize a source that comprises a raw transmission of less than approximately 80% at below approximately 240 nanometers.

Third, the container and/or enclosure is controllably exposed to electromagnetic radiation from, for example, a pulsed UV source for a period of time. While the specific period of time is dependent upon several factors, the preferred total exposure to electromagnetic radiation is less than approximately 30 seconds, and more preferably less than approximately 5 seconds—once again depending upon several factors including the power output of the electromagnetic radiation source, the distance between the container and/or enclosure and the electromagnetic radiation source, the material(s) that the container/enclosure is fabricated from, as well as the desired level of "cleanliness" (i.e. sanitization, sterilization, etcetera) of the container/enclosure—just to name a few factors. It will be understood that the inside and/or outside of the container and/or enclosure can be controllably exposed to the electromagnetic radiation source.

Fourth, the container (preferably the containment region) and/or the enclosure is sanitized and/or sterilized by the electromagnetic radiation. Preferably a 3 Log reduction in undesirable matter in less than approximately 1 to approximately 10 seconds is observed, more preferably a 5 Log reduction in undesirable matter in less than approximately 3 to approximately 20 seconds is observed, and most preferably a 5 Log reduction in undesirable matter in less than approximately 3 seconds is observed.

It will be understood that regardless of it ordinary meaning, the term "undesirable matter" will include microorganisms, bacteria, fungi, and/or any other neutralizable matter that is deemed unacceptable within the containment region of a container in the food and/or beverage industries.

In another embodiment of the present invention, a reflective element 60 is provided which is at least partially introduced within the container during exposure to the electromagnetic radiation source to, in turn, enhance sanitization and/or sterilization of the containment region relative to the same without the reflective element. It will be understood that a substantially spherical reflective element provides heretofore unparalleled performance relative to sanitizing and/or sterilizing areas of the containment region which are otherwise difficult to expose a sufficient concentration of electromagnetic radiation without adversely effecting the container, such as thermal degradation of the same.

It will be understood that the sanitizing and/or sterilizing methods are suitable for use in association with either linear or rotary filler devices. It will be further understood that the terms "sanitizing" and "sterilizing" will be defined herein in accordance with traditional definitions within the food and/or beverage industries.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A method for sanitizing/sterilizing a container for use in the food industry or the beverage industry, comprising the steps of:
    providing a container suitable for filling with at least one of food and beverage, wherein the container comprises:
        a base having an inner surface and an outer surface;
        at least one side wall having an inner surface and an outer surface; and
        a containment region defined by the inner surface of the base and
        the inner surface of the at least one side wall;
    providing an electromagnetic radiation source, wherein the electromagnetic radiation source produces electromagnetic radiation with a wavelength enly between approximately 240 nanometers and approximately 400 nanometers;
    providing a first reflective element positioned above the electromagnetic radiation source;
    providing a second substantially spherical reflective element positioned within the containment region of the container;
    controllably exposing the containment region of the container to electromagnetic radiation from the electromagnetic radiation source for a period of time; and
    at least one of sanitizing and sterilizing the containment region of the container with the electromagnetic radiation.

2. The method according to claim 1, wherein the step of providing an electromagnetic radiation source comprises providing an electromagnetic radiation source which is substantially mercury free.

3. The method according to claim 1, wherein the step of providing an electromagnetic radiation source comprises providing an electromagnetic radiation source which is substantially free from generating ozone during operation of the same.

4. The method according to claim 1, wherein the step of controllably exposing the containment region of the container to electromagnetic radiation for a period of time comprises controllably exposing the containment region to pulsed electromagnetic radiation.

5. The method according to claim 4, wherein the step of controllably exposing the containment region to pulsed electromagnetic radiation comprises exposing the containment region to electromagnetic radiation having a pulse duration of less than approximately 5 milliseconds.

6. The method according to claim 5, wherein the step of controllably exposing the containment region to pulsed electromagnetic radiation comprises exposing the containment region to electromagnetic radiation having a pulse duration of less than approximately 2 milliseconds.

7. The method according to claim 4, wherein the step of controllably exposing the containment region to pulsed electromagnetic radiation comprises exposing the containment region to electromagnetic radiation for a total duration of less than approximately 30 seconds.

8. The method according to claim 4, wherein the step of controllably exposing the containment region to pulsed electromagnetic radiation comprises exposing the containment region to electromagnetic radiation for a total duration of less than approximately 5 seconds.

9. The method according to claim 1, wherein the step of controllably exposing the containment region of the container to electromagnetic radiation for a period of time comprises controllably exposing the containment region to pulsed electromagnetic radiation having a percent transmission of less than approximately 80% at below approximately 240 nanometers.

10. The method according to claim 1, wherein the step of controllably exposing the containment region of the container to electromagnetic radiation for a period of time comprises controllably exposing the containment region to pulsed UV-B electromagnetic radiation.

11. The method according to claim 1, wherein the step of at least one of sanitizing and sterilizing the containment region of the container with the electromagnetic radiation comprises the step of providing a greater than approximately 3 Log reduction in undesirable matter in less than approximately 1 to approximately 10 seconds.

12. The method according to claim 1, wherein the step of at least one of sanitizing and sterilizing the containment region of the container with the electromagnetic radiation comprises the step of providing a greater than approximately 5 Log reduction in undesirable matter in less than approximately 3 to approximately 20 seconds.

13. The method according to claim 1, wherein the step of at least one of sanitizing and sterilizing the containment region of the container with the electromagnetic radiation comprises the step of providing a greater than approximately 5 Log reduction in undesirable matter in less than approximately 3 seconds.

14. A method for sanitizing/sterilizing a container for use in the food industry or the beverage industry, comprising the steps of:
    providing a container suitable for filling with at least one of food and beverage, wherein the container comprises:
        a base having an inner surface and an outer surface;
        at least one side wall having an inner surface and an outer surface;
        a top having an inner surface and an outer surface; and
        a containment region defined by the inner surface of the base,
    the at least one side wall, and the top;
    providing an electromagnetic radiation source, wherein the electromagnetic radiation source produces electromagnetic radiation with a wavelength between approximately 240 nanometers and approximately 400 nanometers;
    providing a first reflective element positioned above the electromagnetic radiation source;

providing a second substantially spherical reflective element positioned within the containment region of the container;

controllably exposing the containment region of the container to pulsed electromagnetic radiation from the electromagnetic radiation source having a pulse duration of less than approximately 5 milliseconds for a total duration of less than approximately 5 seconds; and at least one of sanitizing and sterilizing the containment region of the container with the electromagnetic radiation with a 5 Log reduction in undesirable matter in less than approximately 5 seconds.

15. A method for sanitizing/sterilizing an enclosure associable with a container for use in the food industry or the beverage industry, comprising the steps of:

providing an enclosure associable with a container suitable for filling with at least one of food and beverage, wherein the enclosure consists of:
an inner surface and an outer surface;

providing an electromagnetic radiation source, wherein the electromagnetic radiation source produces electromagnetic radiation with a wavelength only between approximately 240 nanometers and approximately 400 nanometers;

providing a first reflective element positioned above the electromagnetic radiation source;

providing a second substantially spherical reflective element positioned within the containment region of the container;

controllably exposing at least one of the inner surface and the outer surface of the enclosure to electromagnetic radiation from the electromagnetic radiation source for a period of time; and at least one of sanitizing and sterilizing at least one of the inner surface and the outer surface of the enclosure with the electromagnetic radiation.

16. The method according to claim 15, wherein the step of providing an electromagnetic radiation source comprises providing an electromagnetic radiation source which is substantially mercury free.

17. The method according to claim 15, wherein the step of providing an electromagnetic radiation source comprises providing an electromagnetic radiation source which is substantially free from generating ozone during operation of the same.

18. The method according to claim 15, wherein the step of controllably exposing at least one of the inner surface and the outer surface of the enclosure to electromagnetic radiation for a period of time comprises controllably exposing the same to pulsed electromagnetic radiation.

19. The method according to claim 18, wherein the step of controllably exposing at least one of the inner surface and the outer surface of the enclosure to pulsed electromagnetic radiation comprises exposing the same to electromagnetic radiation having a pulse duration of less than approximately 5 milliseconds.

20. The method according to claim 19, wherein the step of controllably exposing at least one of the inner surface and the outer surface of the enclosure to pulsed electromagnetic radiation comprises exposing the same to electromagnetic radiation having a pulse duration of less than approximately 2 milliseconds.

21. The method according to claim 18, wherein the step of controllably exposing at least one of the inner surface and the outer surface of the enclosure to pulsed electromagnetic radiation comprises exposing the same to electromagnetic radiation for a total duration of less than approximately 30 seconds.

22. The method according to claim 18, wherein the step of controllably exposing at least one of the inner surface and the outer surface of the enclosure to pulsed electromagnetic radiation comprises exposing the same to electromagnetic radiation for a total duration of less than approximately 5 seconds.

23. The method according to claim 15, wherein the step of controllably exposing at least one of the inner surface and the outer surface of the enclosure to electromagnetic radiation for a period of time comprises controllably exposing the same to pulsed electromagnetic radiation having a percent transmission of less than approximately 80% at below approximately 240 nanometers.

24. The method according to claim 15, wherein the step of controllably exposing at least one of the inner surface and the outer surface of the enclosure to electromagnetic radiation for a period of time comprises controllably exposing the containment region to pulsed UV-B electromagnetic radiation.

25. The method according to claim 15, wherein the step of at least one of sanitizing and sterilizing at least one of the inner surface and the outer surface of the enclosure with the electromagnetic radiation comprises the step of providing a greater than approximately 3 Log reduction in undesirable matter in less than approximately 1 to approximately 10 seconds.

26. The method according to claim 15, wherein the step of at least one of sanitizing and sterilizing at least one of the inner surface and the outer surface of the enclosure with the electromagnetic radiation comprises the step of providing a greater than approximately 5 Log reduction in undesirable matter in less than approximately 3 to approximately 20 seconds.

27. The method according to claim 15, wherein the step of at least one of sanitizing and sterilizing at least one of the inner surface and the outer surface of the enclosure with the electromagnetic radiation comprises the step of providing a greater than approximately 5 Log reduction in undesirable matter in less than approximately 3 seconds.

28. A method for sanitizing/sterilizing a container and enclosure for use in the food industry or the beverage industry, consisting of the steps of:

providing a container suitable for filling with at least one of food and beverage, wherein the container comprises:
a base having an inner surface and an outer surface;
at least one side wall having an inner surface and an outer surface; and
a containment region defined by the inner surface of the base and
the inner surface of the at least one side wall;

providing an enclosure associable with the container wherein the enclosure comprises:
an inner surface and an outer surface;

providing an electromagnetic radiation source, wherein the electromagnetic radiation source produces electromagnetic radiation with a wavelength between approximately 240 nanometers and approximately 400 nanometers;

providing a first reflective element positioned above the electromagnetic radiation source;

providing a second substantially spherical reflective element positioned within the containment region of the container;

controllably exposing the containment region of the container and at least one of the inner surface and the outer surface of the enclosure to electromagnetic radiation from the electromagnetic radiation source for a period of time; and at least one of sanitizing and sterilizing the containment region of the container and at least one of the inner surface and the outer surface of the enclosure with the electromagnetic radiation.

\* \* \* \* \*